United States Patent [19]

Wagstaff

[11] 4,043,757

[45] Aug. 23, 1977

[54] METHOD FOR DETECTION OF HUMAN MAMMARY CARCINOMA

[75] Inventor: Paul Arlen Wagstaff, Flemington, N.J.

[73] Assignee: Ortho Pharmaceutical Corporation, Raritan, N.J.

[21] Appl. No.: 579,105

[22] Filed: May 20, 1975

[51] Int. Cl.$^2$ .................... G01N 21/08; G01N 33/16
[52] U.S. Cl. ................................. 23/230 B; 424/2; 424/12
[58] Field of Search ............... 424/12, 2; 23/230 B

[56] References Cited

U.S. PATENT DOCUMENTS

| | | | |
|---|---|---|---|
| 3,594,466 | 7/1971 | Guffroy | 424/12 |
| 3,663,684 | 5/1972 | Freedman | 424/12 X |
| 3,840,655 | 10/1974 | Lerner | 424/12 |
| 3,852,415 | 12/1974 | Vandervorde | 424/12 X |
| 3,867,363 | 2/1975 | Hansen | 424/12 X |
| 3,988,115 | 10/1976 | Modabber | 23/230 B |
| 3,999,944 | 12/1976 | Grosser | 23/230 B |

OTHER PUBLICATIONS

Chemical Abstracts, 77:99494p (1972).

Primary Examiner—Sidney Marantz
Attorney, Agent, or Firm—Benjamin F. Lambert

[57] ABSTRACT

A method for detection of human mammary carcinoma in which hypermetabolism of peripheral blood leucocytes is produced by stimulation with mammary tumor antigen, thereby causing greater production of acid metabolites. A greater pH change from alkaline to acid indicates the presence of breast cancer leucocytes and hence of mammary carcinoma.

9 Claims, No Drawings

METHOD FOR DETECTION OF HUMAN MAMMARY CARCINOMA

BACKGROUND OF THE INVENTION

The present invention relates to a method for detection of human mammary carcinoma and more particularly to a method of detecting breast cancer which involves analysis of a blood sample removed from the suspected host.

Cancer in all its various forms is one of the most dreaded diseases of modern times. Not only is it a substantial cause of death, but the disfigurement which may result from its treatment is also greatly feared. No type of cancer produces such fear as cancer of the breast (mammary carcinoma). Unless mammary carcinoma is detected at a very early stage in its development, the general remedy in an attempt to save the life of the patient is a mastectomy, often radical. This operation causes a great deal of trauma in the patient and is not consistently successful, especially where the growth is advanced.

In order to more effectively treat mammary carcinoma and to avoid the necessity for resorting to mastectomy, it is desirable that any such carcinoma be detected as early as possible. Until the development of the present invention, there has not been any wholly satisfactory method for detection of mammary carcinoma, although three methods have been employed.

The oldest method for detection of mammary carcinoma is manual examination of the breast for physical signs of growths, particularly the presence of lumps. Once any such lumps are detected, a biopsy may be performed to determine whether they are benign or malignant. The difficulties associated with this method are well known. First, what must be detected is an abnormal texture of breast tissue. The consistency of breast tissue normally changes during the menstrual cycle and moreover there are individual differences from person to person. In the practice of this prior art method, therefore, it is necessary that the person performing the examination be familiar with the patient. Furthermore, the examination requires a certain amount of skill and is a very subjective one, especially in the early stages of growth. It must be noted that it is impossible to detect a nascent carcinoma by this method because such a growth will not be of sufficient size to be detected.

A second prior art method is that of mammography, a type of soft-tissue X-ray. Again, this method requires subjective interpretation and is useful for detecting only those growths which are sufficiently large to appear on the X-ray plate. Furthermore, this method is inconvenient and expensive, and is therefore likely to be done infrequently, which is undesirable.

The third prior art method is that of thermography, which involves taking a photograph of the breast with infrared-sensitive film to detect any area of abnormal heat output. The theory behind this method is that the carcinoma will produce more heat than the surrounding tissue and will thus be differentiated therefrom in such a photograph. However, as with the prior methods discussed above, the success of this method requires a carcinoma large enough to produce a detectable heat differential. Furthermore, the interpretation of the resultant thermogram requires skill and training.

All of the above-discussed prior art methods for detection of mammary carcinoma suffer from several defects. The most important of these defects is that the methods are successful only for growths which have developed to a size sufficient to be detected in the physical or visual sensing of the method. A further disadvantage is that each method is subjective and requires interpretation of the results by a trained operator. In addition, the above prior art methods do not distinguish between carcinomas and benign growths.

It is therefore an object of the present invention to provide a method for detection of mammary carcinoma which will detect growths of any size, especially growths of a size too small to be detected by the methods of the prior art. It is a further object to provide such a method which does not depend for its result on the interpretation of a highly skilled operator. It is a still further object to provide a method which is convenient to use and relatively inexpensive. These and further objects will become apparent from the reading of the following specification.

SUMMARY OF THE INVENTION

There is provided by the present invention a convenient, sensitive, and objective method for detection of human mammary carcinoma by blood sample analysis. In the method of the invention the peripheral blood leucocytes in the blood sample are stimulated by mammary tumor antigen, which stimulation produces hypermetabolism in breast cancer leucocytes. No such hypermetabolism is produced in non-breast cancer leucocytes. The stimulated breast cancer leucocytes produce more acid metabolites, such as lactic acid, than other leucocytes. This greater production of acid metabolites causes a greater pH change from alkaline to acid to occur only for blood samples containing breast cancer leucocytes and consequently affords a method for detecting mammary carcinoma. The term "breast cancer leucocytes" as used herein means leucocytes of a mammary carcinoma host, at least some of which have been sensitized to mammary carcinoma antigen.

In the method of the invention, peripheral blood leucocytes are isolated from a blood sample (preferably one treated with an anticoagulant such as heparin) by any known technique, e.g., settling with a flocculating agent such as plasma gel. These leucocytes may be purified as is known in the art, or the crude leucocyte fraction may be utilized. The leucocytes or leucocyte fraction is then incubated at ambient or reduced temperature. This incubation may be at a temperature of from about 0° C to about 25° C and should be for a sufficient length of time so that substantially only leucocytes from a mammary carcinoma host yield a positive test result. The preferred incubation conditions are about 0° C to about 25° C for about 5 to 24 hours. The more preferred incubation conditions are at about 5° C for about 10 to 18 hours. Then the incubated leucocyte fraction is mixed with mammary tumor extract (preferably mouse mammary tumor extract) prepared as described below and is incubated while the pH is periodically measured with a pH-detecting means.

It is essential for the method of the invention that the leucocytes or leucocyte fraction be incubated as described above prior to mixing with the mammary tumor extract, because failure to do so causes the test to be non-specific to breast cancer and to yield false positive results for some normal blood samples. The incubated leucocyte fraction and the method of treating human leucocytes so that substantially only those from a mammary carcinoma host are detected by the mammary carcinoma test of the invention are considered to be additional aspects of the present invention.

The incubation after mixing may be at ambient or elevated temperature. It should be understood that the rate at which acid is produced in both the stimulated and unstimulated leucocytes is temperature dependent and increases with increasing temperature. Thus the time interval within which a pH change is expected for a mixture containing breast cancer leucocytes will become smaller with increasing incubation temperature. The preferred incubation temperature is about 25°–40° C, but any temperature which does not destroy the leucocytes or impair the efficacy of the test may be used.

The mammary tumor extract is prepared by homogenizing subcutaneous primary mammary carcinomas, centrifuging a suspension of this homogenized tissue to precipitate the solids, removing the supernatant and sterilizing it by filtration. The filtered extract is then adjusted to a pH of from about 7.1 to about 7.2 and is stored at about 5° C. While mouse mammary tumor extract is preferred, it is envisioned that mammary tumor extract from any source would function in the present invention.

The pH detecting means used in the invention may be of any known in the art, but a chemical pH indicator is preferred. Thus, a mechanical pH detecting device may be used or a chemical pH indicator may be added to the mixture of leucocytes and mammary tumor extract to measure the acid production. If such a chemical indicator is used it should be sensitive to pH changes in the range of from about 6.3 to about 7.4 and thus should have a pKa in this range. The preferred detection range is from about 6.8 to about 7.1. The pH detecting means must also be able to detect pH differences of 0.1 pH unit and preferably 0.05 pH unit within this range.

The preferred pH detecting means is phenol red indicator, which changes from red (alkaline) to yellow (acid) over the pH range 6.8 to 8.4. By comparing the color of a solution of unknown pH with a series of standard solutions, each containing phenol red, it is possible to determine the pH of a test solution to within 0.05 pH units.

Two types of controls are generally employed in the method of the invention. One type (the extract control) is the repetition of the test of the invention using an equivalent protein concentration of a non-cancerous extract, preferably liver extract, in place of the mammary tumor extract. This control measures the tendency of the leucocytes to give a positive result in the absence of stimulation with all other conditions being the same. If this control is positive, then the validity of the corresponding test result is in doubt and both test and control should be repeated. It has been discovered that it is necessary to have a protein extract (the liver extract) in this extract control in order to faithfully duplicate the conditions of the test mixture. In the absence of this protein extract, many positive controls are observed thus reducing the utility of the method of the invention. The second type (the leucocyte control) involves the repetition of the test of the invention using normal leucocytes in place of the breast cancer leucocytes. Comparison of the test results with the results of the leucocyte control should yield a significant difference if the proper pre-mixing incubation of the leucocytes has been performed and if the test sample is from a mammary carcinoma host.

Each batch of tumor extract and non-cancerous protein extract is also tested by repeating the method of the invention for each batch without adding any leucocytes. Only extracts yielding negative results in these tests are used in the method of the invention.

In the method of the invention, the breast cancer leucocytes cause a decrease in the pH of the test solution of at least 0.55 pH units, while non-breast cancer leucocytes cause a reduction of no more than 0.30–0.40 pH units. A positive result in the method of the invention is therefore a reduction in pH of the test sample by at least 0.55 pH units, and preferably by at least 0.60 pH units. These changes occur within 48 hours at about 35° C and within about 5 to 7 days at 25° C.

The method of the invention is illustrated by the following example:

EXAMPLE

Peripheral blood leucocytes are isolated according to the procedure of McCoy with some modifications. All steps are carried out at room temperature using sterile technique. Two ml of plasma gel (obtained from HTI Corporation) is mixed with 10 ml of heparinized whole blood and the mixture is incubated for 1 hour. The upper plasma phase containing the leucocytes is centrifuged at 220 Xg for 20 minutes, and the supernatant is discarded. The leucocyte pellet is triturated with 2 ml of tris buffered ammonium chloride, pH 7.20, and incubated for 10 minutes. The leucocytes are centrifuged at 220 Xg for 5 minutes and the supernatant is again discarded. The leucocyte pellet is washed twice with 2 ml of medium 199 (Flow Laboratories), pH 7.1–7.2, containing penicillin, streptomycin, and phenol red indicator. The resulting leucocyte pellet is resuspended in 2 ml of medium 199 to make the leucocyte suspension to be tested. Then 1/10 ml of this suspension (which suspension contains $1.78 \times 10^6$ leucocytes per ml) is placed in a capped 1 dram glass vial and is incubated for 18 to 20 hours at 5° C.

Mouse mammary tumor extract is then prepared as follows: $CaD_1$ subcutaneous primary mammary carcinomas, 1.0 to 1.5 cm in diameter, from DBA/1J mice (Jackson Laboratories) are excised, pooled, and immediately cut into 1–5 millimeter cubes. Ten ml of tumor tissue is pressed through a 16 gauge stainless steel mesh and is then suspended in 10 ml of medium 199. The carcinoma suspension is centrifuged at 10,000 Xg for 30 minutes at 5° C; the resulting supernatant is removed and is then passed through a 0.45 micron millipore filter. The resulting filtered extract is adjusted to 9.6 mg/ml and to a pH of from about 7.1 to about 7.2 and is stored at 5° C.

To perform the test, 1/10 ml of the extract is added to the vial containing the leucocyte suspension and the resulting mixture is incubated, preferably at 37° C. The mixture is examined for color change due to the pH indicator from red (basic) to yellow (acid) over a period of at least 48 hours, whereby the decrease in pH is measured.

The results of this test on 16 subjects clinically diagnosed as having mammary carcinoma, 7 subjects known to have other neoplastic diseases, and 14 ostensibly normal blood bank samples are shown in Table I. Samples from sixteen subjects gave positive results in the above test, as evidenced by a pH decrease of at least 0.55 pH units. Samples from twenty subjects gave a pH decrease of less than 0.55 pH units, a negative result.

These results are significant to the 99% confidence level.

TABLE I
RESULTS OF MAMMARY CARCINOMA DETECTION TEST

| Clinical Diagnosis of Leucocyte Donor | Results |
|---|---|
| Breast Cancer | 15/16[a] |
| Rectal Cancer | 1/1 |
| Prostatic Cancer | 0/2 |
| Leukemia | 0/1 |
| Fibrocystic Disease | 0/2 |
| Fibrodenoma | 0/1 |
| Normal Blood Bank Donor | 0/14 |

[a]Numerator = Number of Leucocyte Samples Producing a Positive Result
Denominator = Total Number of Samples These results indicate that the test of the invention is useful for specific detection of mammary carcinoma. It detected 96% of the clinically diagnosed mammary carcinoma hosts and yielded only one false positive - the subject with rectal cancer. No false positives were obtained with ostensably normal subjects.

The results of a double blind study on seventeen mammary carcinoma hosts and twenty-three subjects with non-cancerous breast conditions are shown in Table II. The test was conducted as described in the Example, a pH decrease of at least 0.60 pH units being the criterion for a positive result.

TABLE II

| Clinical Diagnosis of Leucocyte Donor | | Results | (%) |
|---|---|---|---|
| Breast Cancer | (<61 yr.) | 7/8[a] | (88%) |
| Control | (<61 yr.) | 1/21 | (5%) |
| Breast Cancer | (>61 yr.) | 3/9 | (33%)[b] |
| Control | (>61 yr.) | 0/2 | (0%) |

[a]Numerator = Number of Leucocyte Samples Producing a Positive Result
Denominator = Total Number of Samples
[b]= Not Significant Due to Small Control Sample Size For reasons not clearly understood at the present time, the method of the invention is of greatest utility in the detection of mammary carcinoma in younger hosts. This fact is illustrated in Table II, in which age 61 was chosen as a dividing line for presentation of results. The results for hosts less than 61 years of age are significant to the 99% confidence level. One false positive was obtained, which may indicate that the particular subject has a mammary carcinoma which is as yet clinically undetectable.

What is claimed is:

1. A method for detecting human mammary carcinoma which comprises the steps of:
   A. separating the leucocytes from a blood sample removed from a suspected mammary carcinoma host;
   B. incubating said leucocytes at a temperature of from about 0° to about 25° C;
   C. mixing said incubated leucocytes with mammary tumor extract; and
   D. incubating said mixture while periodically measuring the pH of said mixture with a pH detecting means.

2. A method as in claim 1 wherein the pH detecting means is a chemical pH indicator having a pKa of from about 6.3 to about 7.4.

3. A method as in claim 2 wherein the chemical pH detecting means has a pKa of from about 6.8 to about 7.1.

4. A method as in claim 3 wherein the chemical pH indicator is phenol red.

5. A method as in claim 1 wherein the leucocytes are incubated for about 5 to about 24 hours.

6. A method as in claim 1 wherein the mixture of incubated leucocytes and mouse mammary tumor extract is maintained at a temperature from about 25° to about 40° C during the interval in which the pH is being measured.

7. A method as in claim 1 wherein the mammary tumor extract is mouse mammary tumor extract.

8. A method as in claim 1 which further comprises the step of identifying mixtures wherein the pH declines by at least 0.55 pH units.

9. The method of claim 5 wherein the incubation of the leucocytes is carried out at a temperature of about 5° C.

* * * * *